United States Patent [19]

Porta et al.

[11] Patent Number: 4,560,455

[45] Date of Patent: Dec. 24, 1985

[54] APPARATUS FOR STERILIZING OBJECTS WITH AN AQUEOUS HYPOCHLORITE SOLUTION

[75] Inventors: Augusto Porta, Carouge, Switzerland; Maurice Schaub, Perrignier; André Ayerbe, Reignier, both of France; Guy Bunter, Carouge, Switzerland

[73] Assignee: Battelle Memorial Institute, Carouge, Switzerland

[21] Appl. No.: 662,309

[22] PCT Filed: Feb. 1, 1984

[86] PCT No.: PCT/EP84/00023

§ 371 Date: Oct. 3, 1984

§ 102(e) Date: Oct. 3, 1984

[87] PCT Pub. No.: WO84/03045

PCT Pub. Date: Aug. 16, 1984

[30] Foreign Application Priority Data

Feb. 3, 1983 [CH] Switzerland ............................ 609/83

[51] Int. Cl.⁴ .......................... C25B 15/08; C25B 9/00

[52] U.S. Cl. .................................. 204/130; 204/237; 204/271; 204/275

[58] Field of Search ............... 204/237, 271, 275, 130, 204/95

[56] References Cited

U.S. PATENT DOCUMENTS

| 1,055,504 | 3/1918 | Albrecht | 204/275 X |
| 3,539,486 | 11/1970 | Fleck | 204/237 X |
| 3,544,442 | 12/1970 | Anderson | 204/271 X |
| 3,819,329 | 6/1974 | Kaestner et al. | 204/271 X |
| 4,419,205 | 12/1983 | Rose | 204/237 X |

Primary Examiner—Donald R. Valentine
Attorney, Agent, or Firm—Karl F. Ross; Herbert Dubno

[57] ABSTRACT

This sterilizing apparatus comports an enclosure (1) in which two electrodes (4,5) of an electrochemical cell are supplied by a transformer-rectifier (16) for producing an aqueous NaOCl solution from a NaCl solution. During its production, the solution is distributed over the surfaces to be sterilized of the objects to be sterilized (9) by a circulation pump (7) and a distribution manifold (6) feeding canes (10) and sprinkling heads (11) by vertical distribution pipes (8).

8 Claims, 2 Drawing Figures

APPARATUS FOR STERILIZING OBJECTS WITH AN AQUEOUS HYPOCHLORITE SOLUTION

CROSS REFERENCE TO RELATED APPLICATIONS

This application is a National Phase application corresponding to PCT/EP84/00023 filed Feb. 1, 1984 and based, in turn, upon the National Application in Switzerland 609/83-2 filed Feb. 3, 1983 under the International Convention.

FIELD OF THE INVENTION

The present invention relates to an apparatus for sterilizing objects with an aqueous hypochlorite solution.

BACKGROUND OF THE INVENTION

There exists on the market a container for sterilizing baby bottles and nipples with an aqueous hypochlorite solution. This container is adapted for receiving baby bottles and nipples the latter being immersed in the hypochlorite solution for at least 90 min, after which the bottles are rinsed with boiled water to remove the taste from this solution. For obtaining adequate sterilization after 90 min, the hypochlorite concentration in the solution should be 125 ppm. It is difficult to reduce this time by increasing the hypochlorite concentration because the hypochlorite taste will then subsist even after rinsing.

Patent application Ser. No. 81/01863 discloses a machine for washing clothes or dishes fitted with an electrochemical cell for producing a hypochlorite solution of desired concentration aimed at providing a bleaching or whitening action. For this, the hypochlorite solution is introduced into the washing bath at a certain concentration and at a desired moment during the washing cycle.

Experiments have been carried out with freshly prepared aqueous hypochlorite solutions from an electrochemical cell which were introduced at a desired concentration into a bath containing baby bottles immersed therein. These experiments have shown that the action of the aqueous hypochlorite solution freshly prepared with an electrochemical cell is similar to that of the hypochlorite sold for sterilizing baby bottles in containers.

By contrast, bewildering results were noted when baby bottles were treated with the hypochlorite solution during the production when this solution after passing it onto the surfaces to be sterilized, was returned to the electrochemical cell for the production of hypochlorite. The hypochlorite concentration of this solution increases progressively during the carrying out of the method.

Comparative testing, the results of which are given hereinafter showed that the destruction of germs with this embodiment is significantly faster and with lower NaOCl concentrations than by immersing baby bottles in a solution of NaOCl obtained by adding into water a concentrated NaOCl solution produced before using it for sterilization. One might explain this surprising result as deriving from the fact that when one uses the NaOCl during the production thereof he takes advantage of the chlorine produced by the electrochemical process which does not instantaneously and completely recombine to provide NaOCl. Yet, the aseptic action of chlorine is known to decreased after recombination of the latter into hypochlorite. This could be the reason why a much faster effect is observed with a solution of extremely weak concentration of NaOCl.

A system has already been proposed in U.S. Pat. No. 3,819,329 in which a bactericidal solution of relatively low pH containing nascent chlorine practically entirely in the form of hypochlorous acid is generated in an electrochemical cell and thereafter distributed on the surfaces to be sterilized. The solution is therefore produced at the desired concentration in the cell and then is dispensed therefrom. Consequently, the production and the use of the solution are not effected together. Now, comparative tests show that the use of NaCl during its production is very important to increase the efficiency of sterilization; this is not possible in the system proposed by this document.

In document GB-A-No. 2,094,992, objects to be sterilized, for instance contact lenses, are dipped into a physiological solution which is subjected to electrolysis so as to obtain a solution of NaOCl. As the dimensions of contact lenses are very small, no distribution means are comtemplated. Since the volume of the necessary solution is very small, the latter is only provided by using two electrodes directly in the cell. Although such a solution is acceptable because of the very small volume of solution to be provided, it is not acceptable when this volume is significantly larger since, there being no agitation, the Faraday yield rapidly decreases due to an electrode polarization phenomenon.

OBJECT OF THE INVENTION

The object of the present invention is to provide a process for sterilizing objects with a hypochlorite solution as it is progressively produced in an electrochemical cell.

Another object of the invention is to provide an improved apparatus for sterilizing objects with an aqueous hypochlorite solution.

SUMMARY OF THE INVENTION

The apparatus of the invention comprises means for continuously circulating an aqueous hypochlorite solution produced in the cell, during the production of the hypochlorite, between the cell and the surfaces of the objects to be sterilized and brought back to the cell. The cell can comprise two electrodes to be connected to a DC current supply, the electrodes being arranged at the bottom of an enclosure comprising rigs for positioning the object to be sterilized above these electrodes. A distribution manifold dispenses the solution against the surfaces of the objects to be sterilized which are not immersed in the solution. A circulating pump has an input connected to the bottom of the enclosure and an output connected to the manifold for dispensing the solution.

The recommended solution enables the use of the hypochlorite as its production progresses. Since the NaOCl is circulated in closed circuit during its production by sprinkling the surfaces to be sterilized, the overall amount of solution is considerably reduced. Besides, such closed circuit recirculation of the NaOCl solution thus produced simultaneously provides a stirring of the liquid in the cell and ensures a high Faraday yield all during the production process.

In addition to an important time economy, the apparatus of the invention enables to effect sterilization with much lower instantaneous hypochlorite concentrations than previously which minimizes the residual final taste of the objects after sterilization and decreases the amount of rinsing when the objects are used for holding foodstuffs or beverages such as feeding and baby bottles.

In view of the speed of the process embodied by the present apparatus, the latter is not limited to sterilizing baby bottles but its use for sterilizing bottles or other containers specific for the food, phamaceutical or cosmetic industry for instance can readily be contemplated.

For the time being, sterilization is thermally achieved in ovens or by injecting water vapor. Such sterilization methods are expensive and the apparatus of the invention can also be used for these cases which enables a significant energy saving.

BRIEF DESCRIPTION OF THE DRAWING

The annexed drawing illustrates schematically and as an Example one embodiment of the apparatus for sterilizing objects of the invention.

SPECIFIC DESCRIPTION

Figures 1, 2:
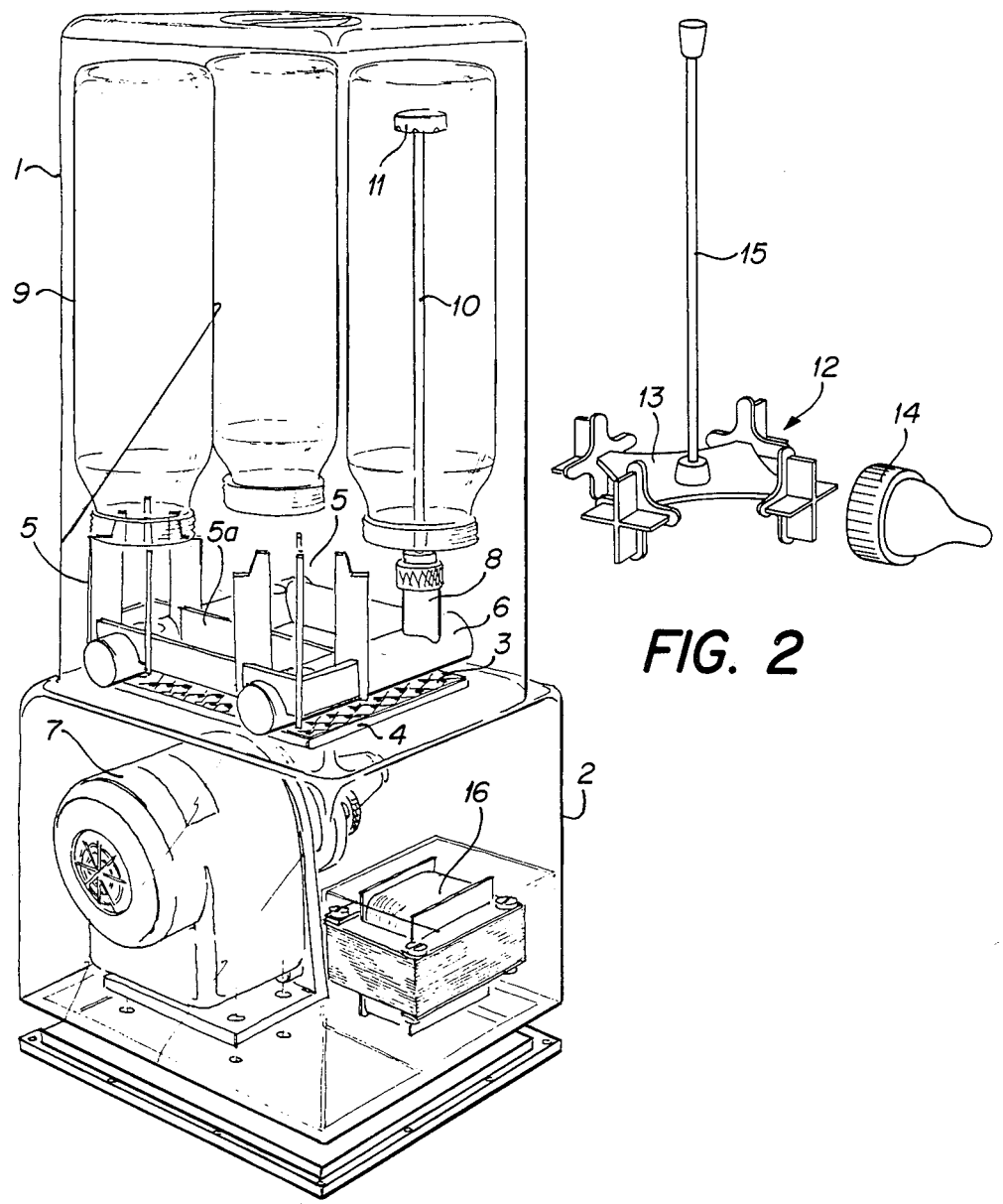
FIG. 1 is a perspective view of the apparatus.
FIG. 2 is a perspective view of a detail shown in FIG. 1.

Although the apparatus to be described, illustrated in this Example, refers to an apparatus for sterilizing baby bottles, it is obvious that one skilled in the art can adapt this appararatus for sterilizing other objects; it is also possible to adapt this apparatus for the continuous treatment of bottles in an installation for washing and sterilizing bottles or other containers for handling foodstuffs, beverages, pharmaceutical and cosmetic products for instance.

This apparatus has an enclosure 1 resting on a stand 2. This enclosure encloses two electrodes 3 and 4 arranged horizontally one above the other in the bottom of enclosure 1. These electrodes are intended to generate an aqueous solution of NaOCl by the electrolysis of an aqueous NaCl solution and are connected to a DC current supply obtained from a transformer rectifier 16 which transforms and rectifies the power from the main. Positioning rigs 5 for holding overturned baby bottles to be sterilized are each constituted by four blades arranged radially in regard to a central axis and at an angle of 90° to each other and located on a dispenser manifold 6 for the hypochlorite solution produced by electrodes 3 and 4. This manifold is connected to the output of a circulating pump 7 for the NaOCl solution, the input of which is connected to the bottom of enclosure 1. This manifold comprises four vertical distributing pipes 8 of which only one is represented and which extend along the vertical axis in the center with respect to the blades of each positionning rig 5. For clarity's sake, only two positionning rigs have been represented. Baby bottles 9 which are to be placed on the two positionning rigs not represented indicate where these rigs are located. The vertical dispensing pipes 8 are prolonged into a hollow cane 10 the end of which is provided with a sprinkling head for distributing the solution under pressure as a shower of streams directed to the bottom of each baby bottle 9.

A nipple holder 12 (FIG. 2) in shape of a four membered star 13 whose ends are for holding the nipples 14 is provided with a vertical stem for handling the holder and remove it from the enclosure 1. The members 13 of the star are fitted to rest on a connecting bracket 5a of the positionning rigs 5 of the bottles 9, i.e. they must stay between these bottles near the bottom of enclosure 1. The nipples 14 are oriented so that their axis of revolution is horizontal not to catch air bubbles.

For sterilizing baby bottles with this apparatus, one introduces the nipple holder 12 and the bottles 9 into enclosure 1 as shown. One introduces 800 ml of water and 6 g of salt into the enclosure, the upper surface of this solution reaching the thread of the bottles and covering the nipples. One connects the electrodes to the transformer-rectifier 16 and, simultaneously, he cuts in the circulation pump 7 for dispensing the solution within the inside of the bottles 7 as the solution of NaCl is progressively transformed by electrolysis into NaOCl. If necessary the external surfaces of the baby bottles can also be sterilized by using, in addition, means for sprinkling said external surfaces with the solution.

A series of comparison tests has been carried out for checking the sterilization efficiency of the apparatus disclosed. The comparative basic test was done with a 125 ppm solution which corresponded to the concentration used in the baby bottle sterilization apparatus commercially available. The water was contaminated with a concentration of $10^8$/ml bacteria of the species Escherichia coli. The immersion treatment lasted for 90 min according to the instructions at room temperature in the order of 20° C. and a pH of 8.7. The sterilization was fully effective. When the solution concentration was decreased to 100 ppm a residual contamination was still present after a 90 min immersion period which showed that the conditions of the previous test were actually borderline for obtaining total sterilization.

Tests were carried out to determine the practical utilization limits of the present apparatus using the same concentration of $10^8$/ml of bacteria Escherichia Coli. The Table below summarizes the results obtained after sprinkling simultaneously 4 baby bottles and their teats.

| Current magnitude (A) | Treatment duration (min) | Sterilization results |
|---|---|---|
| 0.5 | 15 | 0 |
| 0.5 | 10 | 0 |
| 0.5 | 10 | slight contam. |
| 0.5 | 10 | 0 |
| 0.5 | 1 | contam. |
| 0.5 | 2 | 0 |
| 0.25 | 5 | contam. |
| 0.25 | 6 | 0 |

It is noted that reproducible total sterilization is achieved when applying a current in the order of 0.5 A for about 10 min. Following the aspersion of the internal surface of the baby bottles, the concentration of NaOCl of the solution at the end of the treatment was in the order of 30 ppm, instead of 125 ppm although the treatment period was 9 times shorter.

Contrastingly, experiments carried out by means of a hypochlorite solution produced separately by electrolysis, even when using this solution immediately after its preparation, provided results entirely similar to the above-mentioned reference tests achieved with the commercial NaOCl solution and apparatus for sterilizing baby bottles.

This result indicates that it is not the NaOCl production route which is important but the technique consisting in using this NaOCl solution simultaneously while it is generated electrochemically. The design of the apparatus of the invention is specifically intended to enable the simultaneous production of the NaOCl solution and its use for contacting the surfaces to be sterilized, i.e. the bottles and the teats.

Another advantage of the invention comes from the continuous circulation of the solution in contact with the surfaces to be sterilized which enables to considerably lower the overall volume of the solution and, consequently, the required period for attaining the desired concentration. Furthermore, since the solution is produced as sterilization progresses, it is important to have it recirculated which action does not exist with simple immersion.

We claim:

1. A method of sterilizing objects which comprises the steps of:
   positioning said objects within free space in an enclosure directly above a pair of electrodes;
   introducing a sodium chlorite solution into said enclosure to form a solution contacting said electrodes but lying below said objects;
   passing a direct current across said electrode to electrolyse said solution and form hypochlorite therein; and
   continuously during the electrolysis of said solution, pumping hypochlorite-containing solution from the region of said electrodes and dispensing the pumped hypochlorite-containing solution onto exposed surfaces of said objects in said space.

2. An apparatus for the sterilization of objects, comprising:
   an enclosure having a lower portion adapted to receive an aqueous sodium chlorite solution and an upper portion formed with free space;
   a pair of electrodes in said lower portion connectable to a direct current source for electrolysing said solution to form hypochlorite therein directly below said free space;
   means for positioning said objects in said free space directly above said electrodes and at least in part with surfaces of said objects in said free space above the solution in said bottom portion of said enclosure; and
   pump means connected to said bottom portion of said enclosure and provided with means for discharging hypochlorite-containing solution onto surfaces of said objects in said free space.

3. The apparatus defined in claim 2 wherein said electrodes are disposed generally horizontally in said bottom portion of said enclosure and are generally planar.

4. The apparatus defined in claim 3, further comprising a manifold connected to said pump means and provided with discharge elements reaching into said objects for discharging hypochlorite-containing solution into said objects.

5. The apparatus defined in claim 4 wherein said objects are baby bottles and said apparatus further comprises respective rigs extending upwardly from said bottom portion for supporting said baby bottles in an inverted position on said rigs.

6. The apparatus defined in claim 5, further comprising a nipple holder adapted to receive a plurality of nipples and insertable in said enclosure.

7. The apparatus defined in claim 6, further comprising a base carrying said enclosure, said base being provided with a pump forming said pump means and a transformer-rectifier forming said DC supply.

8. A method of operating a sterilizer for objects of the type in which a hypochlorite-containing solution is generated from aqueous sodium chlorite by electrolysis, said method comprising the steps of:
   electrolysing said solution between a pair of horizontal electrodes and a lower portion of an enclosure provided with free space directly above the electrodes and said solution;
   positioning said object in said free space directly above said electrodes; and
   pumping said solution from the region of said electrodes into contact with surfaces of said objects exposed to the free space in said enclosure.

* * * * *

UNITED STATES PATENT AND TRADEMARK OFFICE
CERTIFICATE OF CORRECTION

PATENT NO. : 4,560,455

DATED : 24 December 1985

INVENTOR(S) : Augusto PORTA et al

It is certified that error appears in the above-identified patent and that said Letters Patent is hereby corrected as shown below:

Claim 1, column 5, line 18, change chlorite to chloride;

Claim 2, column 5, line 32, change chlorite to chloride; and

Claim 8, column 6, line 30, change chlorite to chloride.

Signed and Sealed this

Twenty-fifth Day of March 1986

[SEAL]

Attest:

DONALD J. QUIGG

Attesting Officer

Commissioner of Patents and Trademarks